(12) United States Patent
Gao et al.

(10) Patent No.: US 8,079,836 B2
(45) Date of Patent: Dec. 20, 2011

(54) METHOD OF OPERATING A PERISTALTIC PUMP

(75) Inventors: Shawn X. Gao, Irvine, CA (US); David L. Williams, Newport Beach, CA (US)

(73) Assignee: Novartis AG, Lichtstrasse 35, Basel (CH)

( * ) Notice: Subject to any disclaimer, the term of this patent is extended or adjusted under 35 U.S.C. 154(b) by 565 days.

(21) Appl. No.: 11/365,228

(22) Filed: Mar. 1, 2006

(65) Prior Publication Data

US 2007/0207041 A1  Sep. 6, 2007

(51) Int. Cl.
*F04B 43/12* (2006.01)

(52) U.S. Cl. .................. 417/477.2; 417/477.1; 417/476

(58) Field of Classification Search ............ 417/63, 417/476, 474, 477.1, 477.6–477.9, 477.2; 604/30
See application file for complete search history.

(56) References Cited

U.S. PATENT DOCUMENTS

| | | | |
|---|---|---|---|
| 3,173,372 A * | 3/1965 | Baldwin | 417/394 |
| 3,726,613 A * | 4/1973 | von Casimir | 417/477.1 |
| 4,140,118 A | 2/1979 | Jassawalla | |
| 4,187,057 A | 2/1980 | Xanthopoulos | |
| 4,479,761 A | 10/1984 | Bilstad et al. | |
| 4,493,706 A | 1/1985 | Borsanyi et al. | |
| 4,530,647 A | 7/1985 | Uno | |
| 4,537,561 A | 8/1985 | Xanthopoulos | |
| 4,713,051 A | 12/1987 | Steppe et al. | |
| 4,731,057 A | 3/1988 | Tanaka et al. | |
| 4,758,238 A | 7/1988 | Sundblom et al. | |
| 4,768,547 A | 9/1988 | Danby et al. | |
| 4,795,440 A | 1/1989 | Young et al. | |
| 4,798,090 A | 1/1989 | Heath et al. | |
| 4,798,580 A | 1/1989 | DeMeo et al. | |
| 4,838,865 A | 6/1989 | Flank et al. | |
| 4,861,242 A | 8/1989 | Finsterwald | |
| 4,886,431 A | 12/1989 | Soderquist et al. | |
| 4,921,477 A | 5/1990 | Davis | |
| 4,923,375 A | 5/1990 | Ejlersen | |
| 4,935,005 A | 6/1990 | Haines | |
| 4,952,372 A | 8/1990 | Huber | |
| 4,963,131 A | 10/1990 | Wortrich | |
| 4,976,593 A * | 12/1990 | Miyamoto | 417/476 |
| 5,041,096 A * | 8/1991 | Beuchat et al. | 604/118 |
| 5,056,992 A | 10/1991 | Simons et al. | |
| 5,106,366 A | 4/1992 | Steppe | |
| 5,188,604 A | 2/1993 | Orth | |
| 5,195,960 A | 3/1993 | Hossain et al. | |
| 5,207,647 A | 5/1993 | Phelps | |
| 5,217,355 A * | 6/1993 | Hyman et al. | 417/474 |
| 5,267,956 A | 12/1993 | Beuchat | |

(Continued)

FOREIGN PATENT DOCUMENTS

DE  3542454  6/1987

(Continued)

*Primary Examiner* — Devon C Kramer
*Assistant Examiner* — Alexander Comley

(57) ABSTRACT

A method for operating a peristaltic pump having a molded flow channel contained on an elastomeric sheet that is bonded or mechanically attached to a rigid substrate. The pump head rollers are mounted radially from the axis of rotation of the pump motor and compress the elastomeric flow channels against the rigid substrate. During reflux, the pump head is positioned so that at least one of the rollers compresses the elastomeric flow channel at the input end of the peristaltic pump. Such an operation minimizes the amount of the elastomeric sheet that is exposed to high transient pressures.

20 Claims, 2 Drawing Sheets

U.S. PATENT DOCUMENTS

| | | | |
|---|---|---|---|
| 5,302,093 A | 4/1994 | Owens et al. | |
| 5,364,342 A | 11/1994 | Beuchat et al. | |
| 5,403,277 A | 4/1995 | Dodge et al. | |
| 5,429,485 A | 7/1995 | Dodge | |
| 5,429,602 A | 7/1995 | Hauser | |
| 5,460,490 A | 10/1995 | Carr et al. | |
| 5,470,312 A | 11/1995 | Zanger et al. | |
| 5,482,438 A * | 1/1996 | Anderson et al. | 417/44.1 |
| 5,518,378 A | 5/1996 | Neftel et al. | |
| 5,588,815 A | 12/1996 | Zaleski, II | |
| 5,634,907 A * | 6/1997 | Rani et al. | 604/151 |
| 5,709,539 A * | 1/1998 | Hammer et al. | 417/477.3 |
| 5,711,654 A * | 1/1998 | Afflerbaugh | 417/63 |
| 5,746,708 A | 5/1998 | Giesler et al. | |
| 5,746,719 A | 5/1998 | Farra et al. | |
| 5,759,017 A | 6/1998 | Patton et al. | |
| 5,810,204 A | 9/1998 | Devlin et al. | |
| 5,897,524 A * | 4/1999 | Wortrich et al. | 604/30 |
| 5,899,674 A | 5/1999 | Jung et al. | |
| 5,906,598 A | 5/1999 | Giesler et al. | |
| 5,910,110 A * | 6/1999 | Bastable | 600/398 |
| 5,927,956 A | 7/1999 | Lim et al. | |
| 5,928,177 A | 7/1999 | Brugger et al. | |
| 5,996,634 A | 12/1999 | Dennehey et al. | |
| 6,012,999 A | 1/2000 | Patterson | |
| 6,059,544 A | 5/2000 | Jung et al. | |
| 6,099,272 A * | 8/2000 | Armstrong et al. | 417/476 |
| 6,102,678 A * | 8/2000 | Peclat | 417/477.7 |
| 6,129,699 A | 10/2000 | Haight et al. | |
| 6,149,621 A * | 11/2000 | Makihara | 604/27 |
| 6,293,926 B1 | 9/2001 | Sorensen et al. | |
| 6,436,072 B1 | 8/2002 | Kullus et al. | |
| 6,572,349 B2 * | 6/2003 | Sorensen et al. | 417/477.2 |
| 6,962,488 B2 * | 11/2005 | Davis et al. | 417/477.2 |
| 7,104,769 B2 * | 9/2006 | Davis | 417/477.9 |
| 7,393,189 B2 * | 7/2008 | Davis et al. | 417/477.2 |
| 2002/0131881 A1* | 9/2002 | Kagawa et al. | 417/477.1 |
| 2005/0095155 A1 | 5/2005 | Blight et al. | |
| 2005/0186098 A1 | 8/2005 | Davis et al. | |
| 2005/0245888 A1 | 11/2005 | Cull | |
| 2007/0005030 A1 | 1/2007 | Hopkins et al. | |
| 2007/0172368 A1 | 7/2007 | Hopkins et al. | |
| 2007/0217919 A1 | 9/2007 | Sorenson et al. | |
| 2007/0219494 A1 | 9/2007 | Gao et al. | |

FOREIGN PATENT DOCUMENTS

| | | |
|---|---|---|
| DE | 19529894 | 8/1995 |
| EP | 0870925 | 10/1998 |
| EP | 1829568 A1 | 9/2007 |
| EP | 1829568 B1 | 6/2008 |
| FR | 2 466 641 | 4/1981 |
| WO | WO 9318802 | 9/1993 |
| WO | WO 9737703 | 10/1997 |
| WO | WO 03067089 | 5/2003 |

* cited by examiner

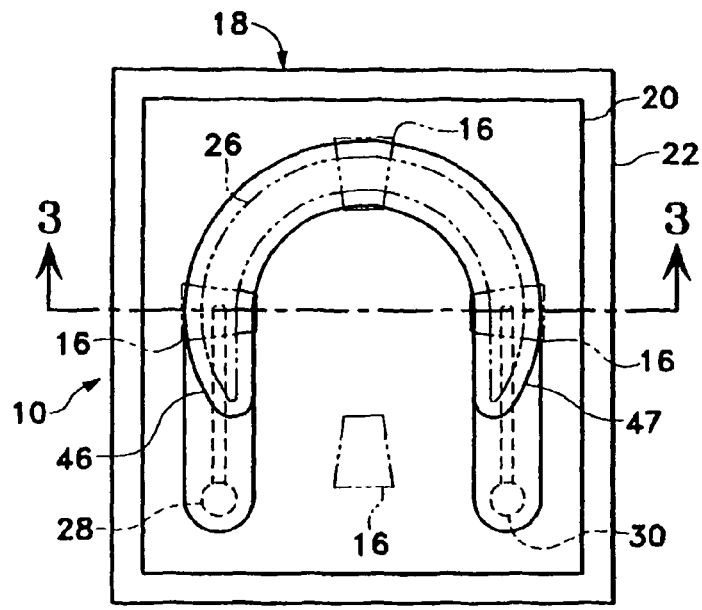
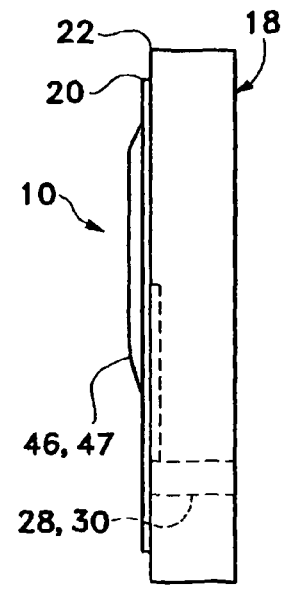
FIG. 1    FIG. 2
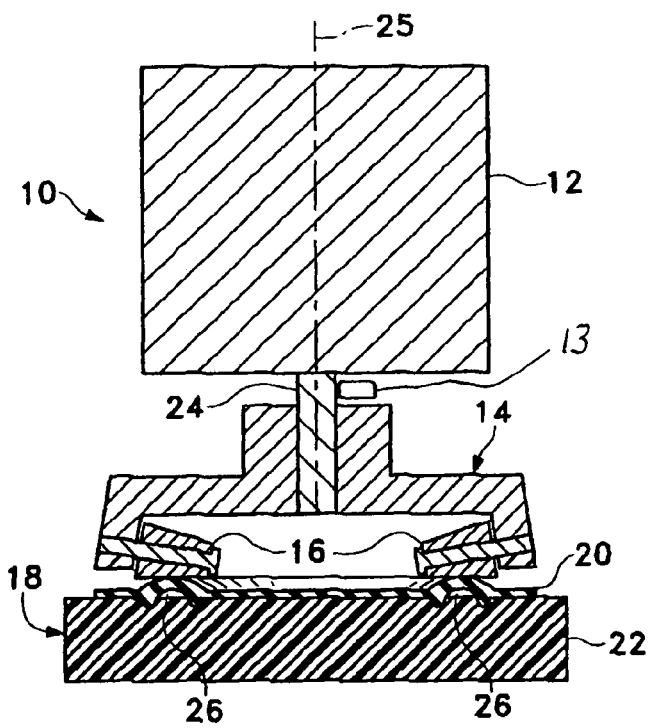
FIG. 3

ND OF OPERATING A PERISTALTIC PUMP

METHOD OF OPERATING A PERISTALTIC PUMP

BACKGROUND OF THE INVENTION

The present invention relates generally to peristaltic pumps and more specifically to peristaltic pumps used in ophthalmic surgical equipment.

Most prior art peristaltic pumps work by compressing or squeezing a length of flexible tubing (sometimes between a fixed race) using a rotating roller head. As the roller head rotates, the rollers pinch off a portion of the tubing and push any fluid trapped in the tubing between the rollers in the direction of rotation. Peristaltic pumps are widely used in medical applications because of their predictable, constant flow properties. These prior art systems, however, typically require manual connection of the pump tube segment around the rotating roller head.

Prior art peristaltic pumps using rotating roller heads also typically impart unwanted pressure pulsations. Several pulsation damping devices have been developed to address this problem (see e.g., U.S. Pat. No. 4,921,477 (Davis)).

With respect to cassettes used in surgical systems having a venturi-type aspiration pump, for the cassette to act as an effective reservoir, the level of fluid (and thus the empty volume) within the cassette must be controlled so that the cassette is neither completely filled nor emptied. If fluid fills the cassette in an aspiration system, fluid may be drawn into the venturi, which would unacceptably interfere with the vacuum level at the surgical instrument. An empty cassette in an aspiration system will result in air being pumped into the drain bag, which would waste valuable reservoir space within the bag. Moreover, constant volume within the cassette in an aspiration system enables more precise control of the level of vacuum within the surgical instrument.

Additionally, the size of the reservoir within the cassette affects the response time of the cassette. A larger reservoir provides more storage capacity but slows the response time of the system. A smaller reservoir increases the response time of the system, but may not have adequate storage capacity. This dilemma has been addressed by cassettes that have two internal reservoirs. Such a cassette is illustrated in U.S. Pat. No. 4,758,238 (Sundblom, et al.) (the "Sundblom Cassette"). The smaller reservoir is in direct fluid communication with the surgical handpiece while a larger reservoir is positioned between the smaller reservoir and the source of vacuum. This allows for a faster response time and larger storage capacity. The smaller reservoir, however, must be periodically emptied into the larger reservoir prior to the smaller reservoir filling up. This requires that the vacuum to the smaller reservoir be closed prior to opening the drain to the larger reservoir. Closing the vacuum line to the small reservoir requires that the surgical procedure be stopped during drainage of the smaller reservoir.

Another system, described in U.S. Pat. No. 5,899,674 (Jung, et al.) uses a venturi pump to provide aspiration vacuum and a separate peristaltic pump located between the large reservoir and the small reservoir. The peristaltic pump is used to actively pump the fluid from the small reservoir into the small reservoir when the small reservoir becomes full. Such a system allows for the continued operation of the system during drainage of the small reservoir.

Another prior art pump is disclosed in U.S. Pat. No. 6,293,926 B1 (Sorensen, et al.) that describes a peristaltic pump having a molded flow channel contained on an elastomeric sheet that is bonded or mechanically attached to a rigid substrate. The pump head rollers are mounted radially from the axis of rotation of the pump motor and compress the elastomeric flow channels against the rigid substrate. The commercial embodiment of the invention described in this patent is sold as the INFINITI® Vision System by Alcon Laboratories, Inc., Fort Worth, Tex. This surgical console uses a Fluid Management System or cassette wherein the elastomeric sheet is friction fit into the rigid substrate without the use of any adhesives Such a construction method has proven to be extremely reliable, but this commercial system is intended primarily for cataract surgery and has no other source of vacuum other than the peristaltic pump. Therefore, the fluidic system is exposed primarily to negative pressure or vacuum and is not exposed to transient high positive pressures, such as are encountered during a reflux operation in posterior segment surgical procedures using a venturi pump as the primary source of vacuum. High positive pressures have the potential to cause failure at the elastomer/substrate interface if a friction fit construction technique is used.

Accordingly, a need continues to exist for a method of operating a peristaltic pump that reduces the potential for cassette failure under transient positive pressures.

BRIEF SUMMARY OF THE INVENTION

The present invention improves upon prior art peristaltic pumps by providing a method for operating a peristaltic pump having a molded flow channel contained on an elastomeric sheet that is bonded or mechanically attached to a rigid substrate. The pump head rollers are mounted radially from the axis of rotation of the pump motor and compress the elastomeric flow channels against the rigid substrate. During reflux, the pump head is positioned so that at least one of the rollers compresses the elastomeric flow channel at the input end of the peristaltic pump. Such an operation minimizes the amount of the elastomeric sheet that is exposed to high transient pressures.

One objective of the present invention is to provide a peristaltic pump that uses molded elastomeric flow channels.

Another objective of the present invention is to provide a peristaltic pump having radially oriented pump rollers.

Yet another objective of the present invention is to provide a peristaltic pump having pump rollers that compress elastomeric flow channels against a rigid substrate.

Still another objective of the present invention is to provide a peristaltic pumping system wherein the pump rollers are parked so as to isolate the pump fluid channel from transient high positive pressures.

These and other advantages and objectives of the present invention will become apparent from the detailed description, drawings and claims that follow.

BRIEF DESCRIPTION OF THE DRAWINGS

FIG. 1 is a schematic top plan view of a peristaltic pump that may be used with the present invention, with the motor and roller head removed for clarity.

FIG. 2 is a schematic side elevational view of a peristaltic pump that may be used with the present invention, with the motor and roller head removed for clarity.

FIG. 3 is a cross-sectional view of a peristaltic pump that may be used with the present invention taken at line 3-3 in FIG. 1.

DETAILED DESCRIPTION OF THE INVENTION

Figure 4:
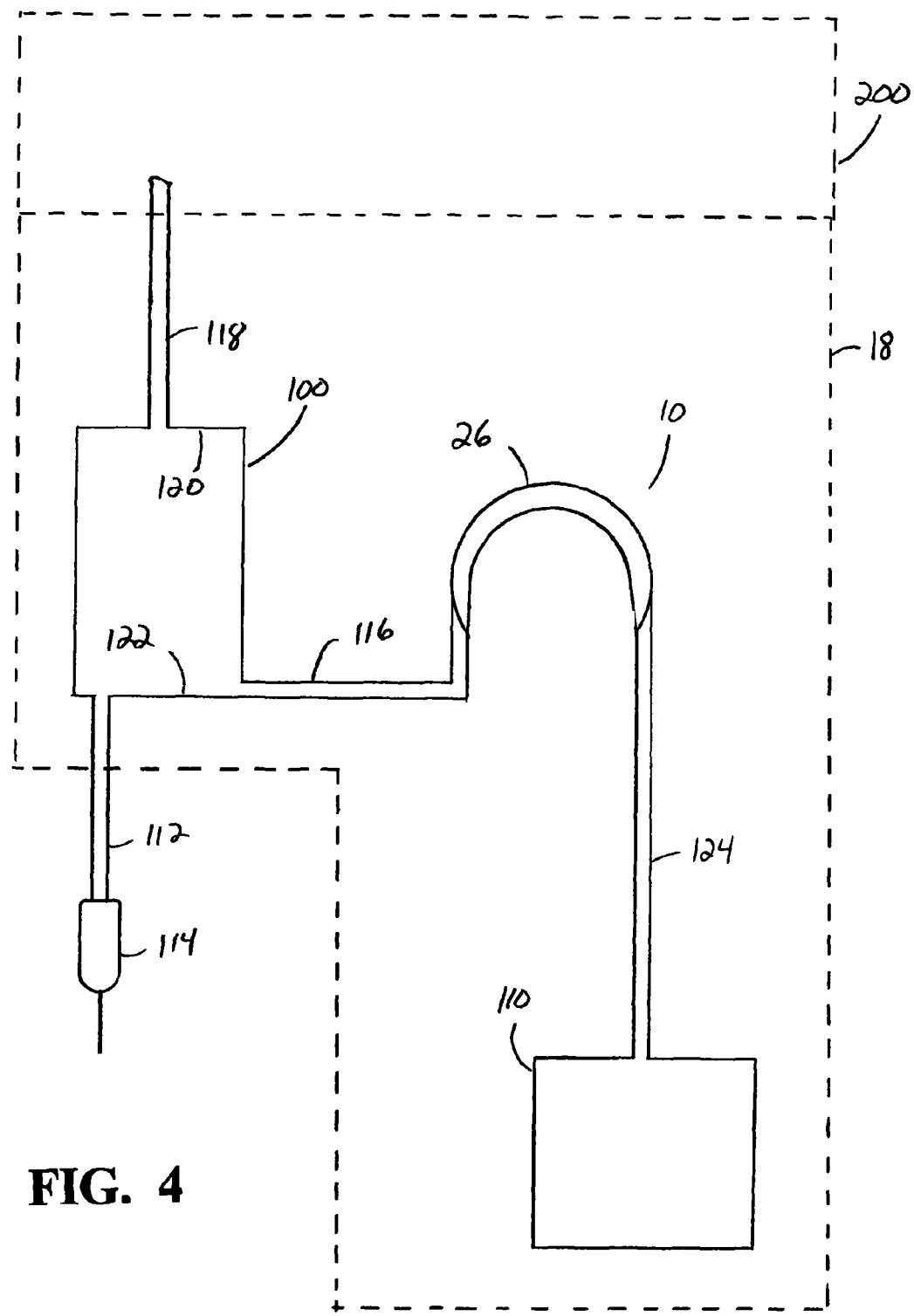
FIG. 4 is a schematical view of a cassette that that may be used with the present invention.

As best seen in FIGS. 1, 2 and 3, peristaltic pump 10 that may be used with the present invention generally includes pump motor 12, roller head 14, containing one or more rollers 16 and cassette 18 having elastomeric sheet 20 applied to the exterior of relatively rigid body or substrate 22. Pump motor 12 preferably is a stepper or D.C. servo motor. Roller head 14 is attached to shaft 24 of motor 12 so that motor 12 rotates roller head 14 in a plane generally normal to the axis of shaft 24, and the longitudinal axes of rollers 16 are generally radial to the axis of shaft 24. Motor 12 contains encoder 13, which may be located on shaft 24 that provides rotational location information for shaft 24. As the position of rollers 16 is fixed relative to shaft 24, information regarding the rotational information of shaft 24 also locates rollers 16. Pump motor 12, roller head 14, roller 16 and encoder 13 are generally located within surgical console 200, represented schematically only in FIG. 4. Surgical console 200 contains sufficient hardware and software to process signals from encoder 13 and control motor 12. Suitable hardware and software is well-known to those skilled in the art and one suitable console is the ACCU-RUS® surgical system available from Alcon Laboratories, Inc., Fort Worth, Tex.

Sheet 20 contains molded fluid channel 26 that is generally planar, arcuate in shape (within the plane) and having a radius approximating that of rollers 16 about shaft 24. Fluid channel 26 fluidly connects ports 28 and 30. Sheet 20 may be made of any suitably flexible, easily molded material such as silicone rubber or thermoplastic elastomer. Sheet 20 is attached or bonded to substrate 22 by any suitable technique such as adhesive, heat fusion or mechanical crimping. Substrate 22 preferably is made of a material that is rigid with respect to sheet 20, such as a rigid thermoplastic, and may be made by any suitable method, such as machining or injection molding. Cassette 18 is generally formed separately from console 200 and held in operative association with console 200 by fluid connections and latching mechanisms well-known in the art.

In use, cassette 18 is held in close proximity to roller head 14 so that rollers 16 compress channel 26 against substrate 22 as roller head 14 rotates. The longitudinal axes of the rollers are arranged so that rollers 16 contact with channel 26 is generally parallel with the plane of channel 26. Such an arrangement eliminates the need to loop a length of flexible tubing over the pump roller head and thus simplifies the loading of pump channel 26 against pump roller head 14. Rollers 16 may be tapered along their axial length to accommodate the difference in path length traveled by the inner and outer sections of rollers 16 as roller head 14 rotates. Unwanted pressure pulsations could be minimized by providing channel transition regions 46 and 47 having internal cross-sections that taper from zero to the full cross-section of channel 26. These regions minimize the abrupt change in displaced volume as rollers 16 transition on or off of channel 26.

As best seen in FIG. 4, cassette 18 further include reservoir 100 and drain bag 110. Reservoir 100 is connected to surgical handpiece 112 through aspiration line 114 and connected to peristaltic pump 10 through pump inlet line 116. Vacuum line 118 enters reservoir 100 near top 120 of reservoir 100 and is connected to a source of vacuum, such as a venturi pump (not shown), contained within console 200. When vacuum is applied to vacuum line 118, such vacuum is communicated to reservoir 100; thereby drawing fluid through handpiece 114 via aspiration line 112. When reservoir 100 becomes sufficiently filled with fluid, peristaltic pump 10 is activated to draw fluid off of bottom 122 of reservoir 100 through pump inlet line 116 and port 28 and discharges the excess fluid into drain bag 110 through port 30 and pump discharge line 124.

During use, instead of a vacuum being applied to vacuum line 118, a transient high positive pressure may be applied. For example, during a reflux operation. This positive pressure is transmitted to peristaltic pump 10 through pump inlet line 116. If sufficient positive pressure is transmitted to peristaltic pump 10, sheet 20 may become dislodged from substrate 22, thereby destroying the fluidic integrity of cassette 18. In order to avoid high pressure spike from entering fluid channel 26, when pressure is applied to line 118, console 200 also directs motor 12 to stop and park rollers 16 so that one roller 16 pinches shut fluid channel 26 near port 28, as shown in FIGS. 1 and 3. The location of rollers 16 can be accurately predicted because of the position sensor 13. Parking roller 16 at such a location essentially acts like a shut off valve to prevent any transient pressure spikes from entering fluid channel 26.

This description is given for purposes of illustration and explanation. It will be apparent to those skilled in the relevant art that modifications may be made to the invention as herein described without departing from its scope or spirit.

We claim:

1. A method for operating a peristaltic pump having a roller head, comprising:
    operatively contacting a cassette with at least one roller of the roller head, the cassette having a body and an elastomeric sheet coupled to the body, wherein a space between the body and the sheet forms at least one fluid channel;
    rotating the roller head so that the roller head contacts the sheet to cause fluid flow through the at least one fluid channel, wherein rotating the roller head displaces the elastomeric sheet to move fluid between the sheet and the body;
    determining a location of the at least one roller; and
    parking the at least one roller at an inlet port that inhibits fluid flow through the at least one fluid channel to protect the fluid channel from a positive pressure, the parked position of the at least one roller being based upon the determined location of the at least one roller;
    applying the positive pressure to a vacuum line;
    a surgical console determining when a positive pressure is being or will be applied to the vacuum line coupled to the at least one fluid channel and wherein parking the at least one roller is in response to the surgical console determination that a positive pressure is being or will be applied to the vacuum line.

2. The method of claim 1, wherein the at least one fluid channel forms part of a fluid path between a fluid reservoir and a drain bag.

3. The method of claim 1, wherein parking the at least one roller in the parked position isolates the at least one fluid channel from a transient high pressure.

4. The method of claim 1, wherein the parked position is on the inlet port of the at least one fluid channel to reduce exposure of the sheet to a transient high positive pressure when the at least one roller is in the parked position.

5. The method of claim 1,
    wherein the sheet comprises a planar portion and a raised portion in the planar portion and wherein a space between the body and the raised portion of the sheet forms the at least one fluid channel; and
    wherein rotating the roller head to cause fluid flow comprises rotating the roller head so that the roller head contacts the raised portion of the sheet to cause fluid flow through the at least one fluid channel.

6. The method of claim 5, wherein the at least one fluid channel formed between the raised portion of the sheet and the body comprises at least one transition region having an internal cross section that tapers from a reduced cross section of the at least one fluid channel to a full cross section of the at least one fluid channel.

7. The method of claim 1, wherein determining a location of the at least one roller comprises continuously determining a location of the at least one roller.

8. The method of claim 1, wherein the at least one roller is tapered along an axial length of the at least one roller to accommodate a difference in path length traveled by inner and outer sections of the at least one roller.

9. A system, comprising:
a surgical console comprising:
a peristaltic pump having a roller head; and
an encoder operable to provide rotational location information for the peristaltic pump;
a surgical cassette comprising:
a body; and
an elastomeric sheet comprising:
a planar portion; and
a raised portion in the planar portion;
wherein the sheet is coupled to the body and wherein a space between the body and the raised portion of the sheet forms at least one fluid channel such that fluid in the at least one fluid channel is in contact with at least a portion of the sheet;
wherein the surgical console is configured to receive the surgical cassette, and wherein at least one roller of the roller head is configured to contact the raised portion of the sheet of the surgical cassette when the surgical cassette is received in the surgical console, wherein rotating the roller head displaces the elastomeric sheet to move the fluid between the sheet and the body;
wherein rotation of the at least one roller in contact with the raised portion of the sheet causes fluid flow through the at least one fluid channel;
wherein the surgical console is configured to perform a reflux operation by applying a positive pressure to a vacuum line coupled to the at least one channel;
wherein the surgical console is configured to park the at least one roller near an inlet port in a position that inhibits fluid flow through the at least one fluid channel, the parked position of the at least one roller being determined using the rotational location information from the encoder; and
wherein the surgical console is configured to apply the positive pressure to the vacuum line;
wherein the roller is parked on the elastomeric sheet at an entrance location to at least partially block positive pressure experienced in a vacuum line, coupled to the fluid channel, in response to a surgical console determination that a positive pressure is being or will be applied to the vacuum line.

10. The system of claim 9, wherein the at least one fluid channel forms part of a fluid path between a fluid reservoir and a drain bag.

11. The system of claim 9, wherein parking the at least one roller in the parked position isolates the at least one fluid channel from a transient high pressure.

12. The system of claim 9, wherein the parked position is on an inlet port of the at least one fluid channel to reduce exposure of the raised portion of the sheet to a transient high positive pressure when the at least one roller is in the parked position.

13. The system of claim 9, wherein the rotational location information from the encoder is used by the system to determine a location of the at least one roller.

14. The system of claim 9, wherein the at least one roller is tapered along an axial length of the at least one roller to accommodate a difference in path length traveled by inner and outer sections of the at least one roller.

15. The system of claim 9, wherein the at least one fluid channel formed between the raised portion of the sheet and the body comprises at least one transition region having an internal cross section that tapers from a reduced cross section of the at least one fluid channel to a full cross section of the at least one fluid channel.

16. A method for operating a peristaltic pump having a roller head carrying a plurality of rollers, comprising:
operatively placing the roller head in contact with a flexible fluid channel;
rotating the roller head so that the plurality of rollers contact the fluid channel and cause fluid flow through the fluid channel;
determining a location of the rollers; and
stopping the rollers at an inlet position of the fluid channel, based upon the determined location of the rollers;
wherein the flexible fluid channel is provided by a cassette, the cassette having a body and an elastomeric sheet attached to the body, the sheet containing at least one molded fluid channel, and wherein stopping the rollers comprises parking at least one roller in a parked position at an inlet port to the fluid channel to pinch the elastomeric sheet against the body to close the fluid channel to act as a shut off valve to prevent fluid entering the channel and to isolate the fluid channel from positive pressure to prevent any transient pressure spikes from entering the fluid channel;
a surgical console determining when a positive pressure is being or will be applied to a vacuum line coupled to the fluid channel and wherein stopping the rollers is in response to the surgical console determination that a positive pressure is being or will be applied to the vacuum line.

17. The method of claim 16, wherein the peristaltic pump is spaced between a fluid reservoir and a drain bag.

18. The system of claim 9, further comprising a reservoir coupled to the peristaltic pump, the vacuum line, and a handpiece through an aspiration line, wherein the peristaltic pump is configured to pump excess fluid out of the reservoir.

19. The system of claim 18, wherein the vacuum line is coupled to a separate source of vacuum and wherein during the reflux operation, a positive pressure is applied to the reservoir through the vacuum line.

20. The method of claim 1, further comprising pulling a vacuum, by a separate vacuum source, through the vacuum line on a reservoir coupled to the at least one fluid channel and a handpiece through an aspiration line.

* * * * *